United States Patent [19]

Jones et al.

[11] 4,114,275
[45] Sep. 19, 1978

[54] FOOT CONTROLLER APPARATUS FOR AIR DRIVEN DENTAL HANDPIECES OR THE LIKE

[75] Inventors: Arthur Lee Jones; Dennis Frank Leffler, both of Charlotte, N.C.

[73] Assignee: Pelton & Crane Company, Charlotte, N.C.

[21] Appl. No.: 741,383

[22] Filed: Nov. 12, 1976

[51] Int. Cl.² ............................................. A61C 19/02
[52] U.S. Cl. ................................... 32/22; 32/DIG. 3
[58] Field of Search ................. 318/551; 251/295, 57, 251/61.2; 32/22, 27, DIG. 3

[56] References Cited

U.S. PATENT DOCUMENTS

| 3,842,504 | 10/1974 | Ricks | 251/57 |
| 3,855,704 | 12/1974 | Booth | 32/28 |

Primary Examiner—Robert Peshock
Attorney, Agent, or Firm—Bell, Seltzer, Park & Gibson

[57] ABSTRACT

Foot controller apparatus is characterized by providing for remote foot control by a minimum size foot pedal device of the flow of compressed air to an air driven dental handpiece or the like without the necessity of bulky air lines passing through or the incorporation of complicated electrical or mechanical mechanisms in the foot pedal device, as follows. An outwardly biased, depressible foot pedal device includes a diaphragm therein for forming an air sealed chamber which reduces in volume upon depression of the foot pedal device and conveys an air flow through an elongate tube to a diaphragm operated, air modulating, regulator valve positioned away from the foot pedal device and in the compressed air conduit leading to the dental handpiece for pneumatically operating the valve to control the flow of compressed air to the dental handpiece for driving same. The apparatus may also preferably include a diaphragm operated electrical switch mechanism electrically connected with electrically operated valves in chip air and coolant water conduits to the handpiece and with the foot pedal air tube for being pneumatically operated by the foot pedal device for controlling the flow of chip air and coolant water through the dental handpiece.

9 Claims, 9 Drawing Figures

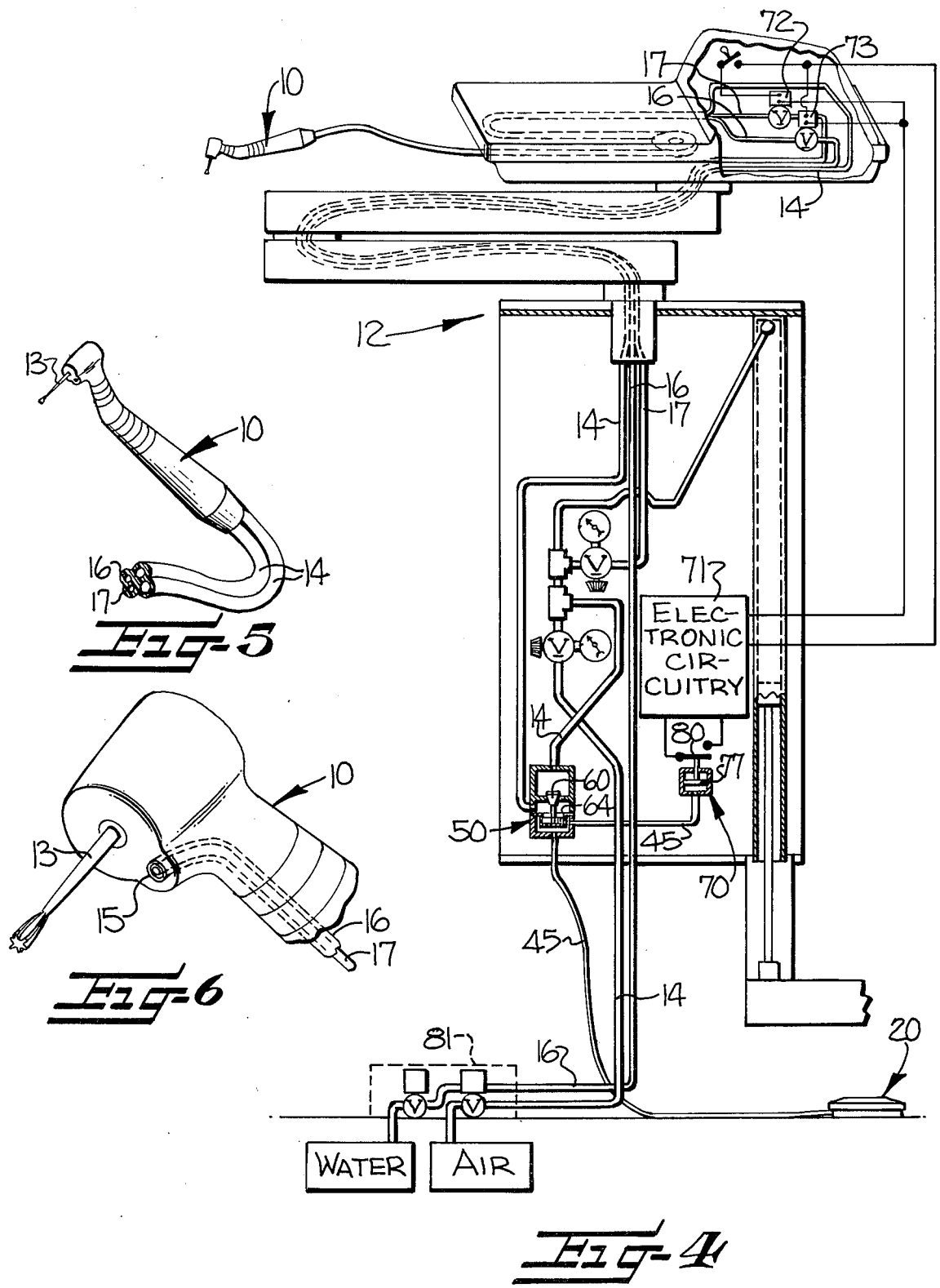

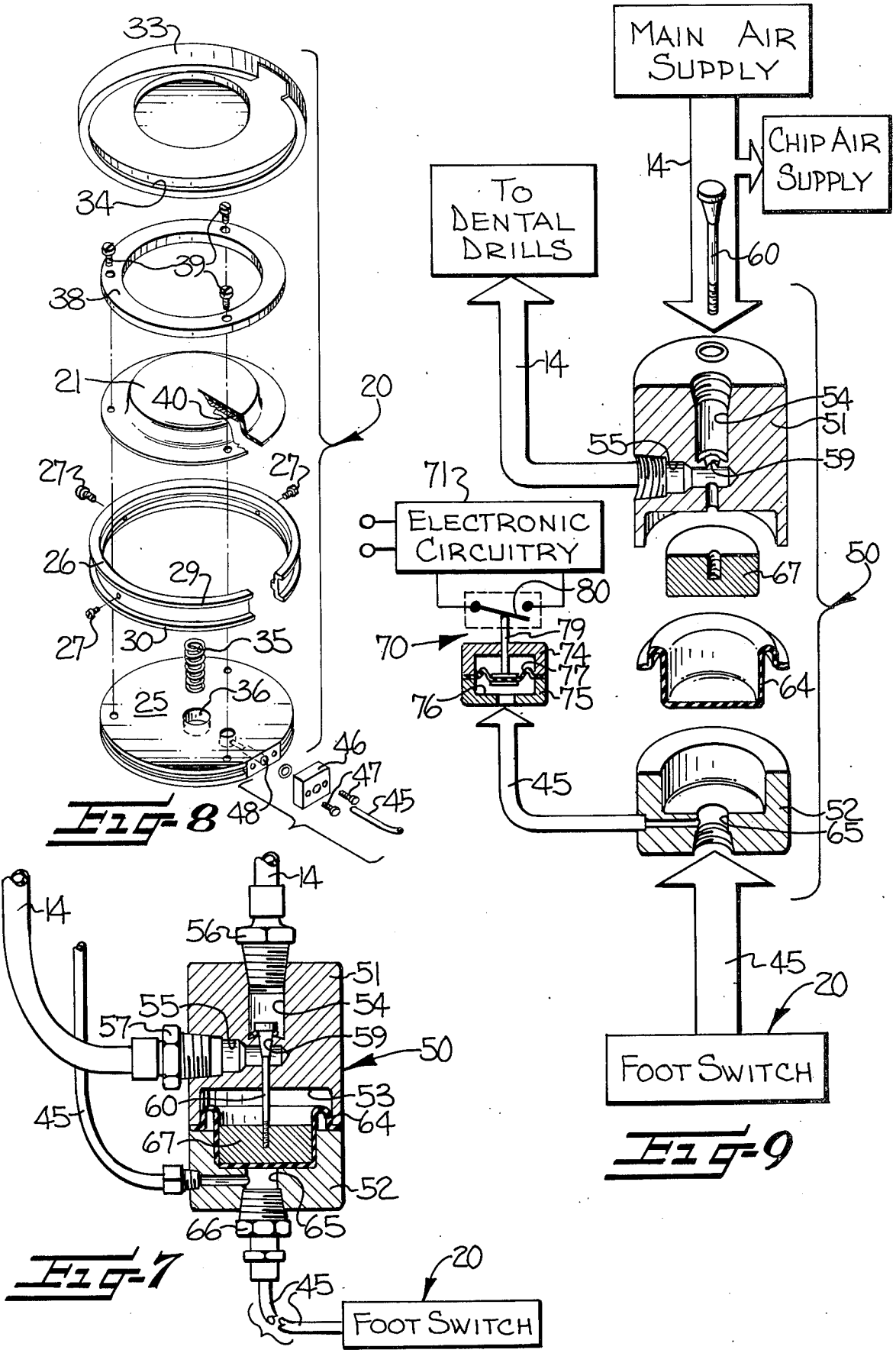

FOOT CONTROLLER APPARATUS FOR AIR DRIVEN DENTAL HANDPIECES OR THE LIKE

This invention relates to a foot controller apparatus for manually controlling the supply of compressed air to an air driven dental handpiece or the like, and preferably also for controlling the flow of coolant water and chip air through the handpiece, and being characterized by a construction providing for remote foot control by a minimum size foot pedal device without the necessity of bulky compressed air lines or water lines passing through the foot pedal device or in the incorporation of complicated electrical or mechanical mechanisms in the foot pedal device.

BACKGROUND OF THE INVENTION

Dental handpieces, such as drills and the like, and other medical or treatment hand instruments are often driven by compressed air. The drive air for such handpieces has been conventionally controlled in part by a foot controller mechanism conveniently placed on the floor next to a treatment chair containing a patient for operation by the foot of a dentist or other person treating the patient to leave the hands free for treatment of the patient. These foot controllers are utilized to control the amount of drive air transmitted to the handpiece for controlling the speed of operation of the handpiece. Additionally, air driven dental drill handpieces often have provisions therein for emitting coolant water and chip air for cleaning of debris from the teeth of a patient following the drilling operation performed by the handpiece. Foot controllers have also been utilized for controlling such coolant water and chip air through the dental handpiece.

Present foot controller mechanisms are more conventionally direct acting in that the compressed air which drives the air driven handpiece goes into the foot controller and is regulated at that point by the foot controller for providing a desired flow of compressed air to the handpiece. Also, switches are activated in the foot controller to turn on and off the coolant water and chip air. Thus, the more conventional foot controllers are, of necessity, fairly large devices in that they must contain the regulator valves, switches and associated plumbing for the drive air, and chip air and coolant water when utilized. The conduits to and from these foot controllers must be fairly large to contain sufficiently sized air lines in and out of the foot controllers for accommodating the amount of compressed air necessary for the handpiece. Accordingly, the dentists or operators have found these foot controllers and associated conduits to be burdensome and a hindrance to their mobility due to the size and bulk, etc. thereof.

Although foot controllers have been suggested which do not include the large conduits and air regulators directly in the foot controller and attempt to remotely control such air regulator devices positioned at a distant location, these foot controllers for remotely controlling the drive air, and the chip air and coolant water when utilized, have been complicated in design, subject to malfunctioning and required considerable maintenance due to the complicated electrical or mechanical mechanisms contained within the foot controller device.

OBJECTS AND SUMMARY OF THE INVENTION

Accordingly, it is the object of this invention to provide an improved foot controller apparatus for manually controlling the supply of compressed air to an air driven dental handpiece or the like, and for controlling the supply of chip air and coolant water to the dental handpiece if utilized, which overcomes problems presented by prior foot controllers.

It is a more specific object of this invention to provide such an improved foot controller apparatus which is characterized by a construction providing for remote foot control by a minimum size foot pedal device of the flow of the compressed air from a supply, through an air conduit, to the handpiece for driving same, and for controlling the supply of chip air and coolant water to the handpiece if utilized, without the necessity of bulky compressed air lins passing through the foot pedal device or the incorporation of complicated electrical or mechanical mechanisms in the foot pedal device.

It has been found by this invention that the above objects may be accomplished by providing a foot controller apparatus including generally the following mechanisms.

An outwardly biased, depressible foot pedal device of minimum size for easy contact by the foot of an operator of the dental handpiece is provided which defines therewithin a hollow cavity having a diaphragm means therein for forming an air sealed chamber which reduces in volume upon depression of the foot pedal device.

An elongate tube of smaller cross-sectional dimensions than the compressed air conduit necessary for conveying compressed air to the dental handpiece is provided which is connected at one end thereof with the foot pedal device and communicates with the air sealed chamber for conveying an air flow therethrough resulting from operation of the foot pedal device.

A diaphragm operated, air modulating, regulator valve means is positioned away from the foot pedal device to avoid interference with the operator of the dental handpiece and is positioned in the compressed air conduit leading to the dental handpiece. The diaphragm operated valve means is connected with the other end of the air tube for being pneumatically operated by the flow of air through the air tube resulting from foot operation of the foot pedal device for controlling the flow of compressed air to the dental handpiece for driving same.

In the event the dental handpiece includes means for emitting chip air and coolant water including a water supply, a conduit for conveying coolant water to the handpiece, a separate conduit for conveying chip air to the handpiece and electrically operated valve means in the chip air conduit and the coolant water conduit, this invention further provides the following mechanisms.

A diaphragm operated electrical switch means is positioned away from the foot pedal device to avoid interference with the operator of the dental handpiece and is electrically connected with the electrically operated valve means in the chip air and coolant water conduits. The diaphragm operated switch means is connected with the foot pedal air tube for being pneumatically operated by a flow of air through the air tube resulting from foot operation of the foot pedal device for electrically operating the valve means to control the flow of chip air and coolant water to the dental handpiece.

Thus, the present invention overcomes problems presented by prior foot controller mechanisms by providing improved foot controller apparatus having a foot pedal device of minimum size including a diaphragm mechanism therein for creating a flow of air through a small tube to remotely positioned diaphragm operated air modulating regulator valve for the handpiece drive air and to a diaphragm operated electrical switch means for the chip air and coolant water. Accordingly, bulky plumbing and complicated electrical and mechanical mechanism are eliminated from the foot pedal device.

BRIEF DESCRIPTION OF DRAWINGS

Some of the objects and advantages of the invention having been stated, other objects and advantages will appear when taken in conjunction with the accompanying drawings, in which:

FIG. 1 is a perspective view illustrating the use of the foot controller apparatus of this invention for manually controlling dental handpieces or the like;

FIG. 4 is a diagrammatic view illustrating the use of the foot controller apparatus of this invention for controlling a dental handpiece or the like;

FIG. 5 is an enlarged perspective view of a dental handpiece which may be controlled by the foot controller apparatus of this invention;

FIG. 6 is an enlarged perspective view of the head of the dental handpiece of FIG. 5;

FIG. 7 is a cross-sectional view of the diaphragm operated, air modulating, regulator valve utilized with the foot controller apparatus;

FIG. 8 is an exploded view of the foot pedal device of FIGS. 2 and 3; and

FIG. 9 is an exploded, sectional, partly diagrammatic view, particularly illustrating the construction of the regulator valve utilized with the foot controller apparatus of this invention.

DESCRIPTION OF PREFERRED EMBODIMENT

Figure 1:
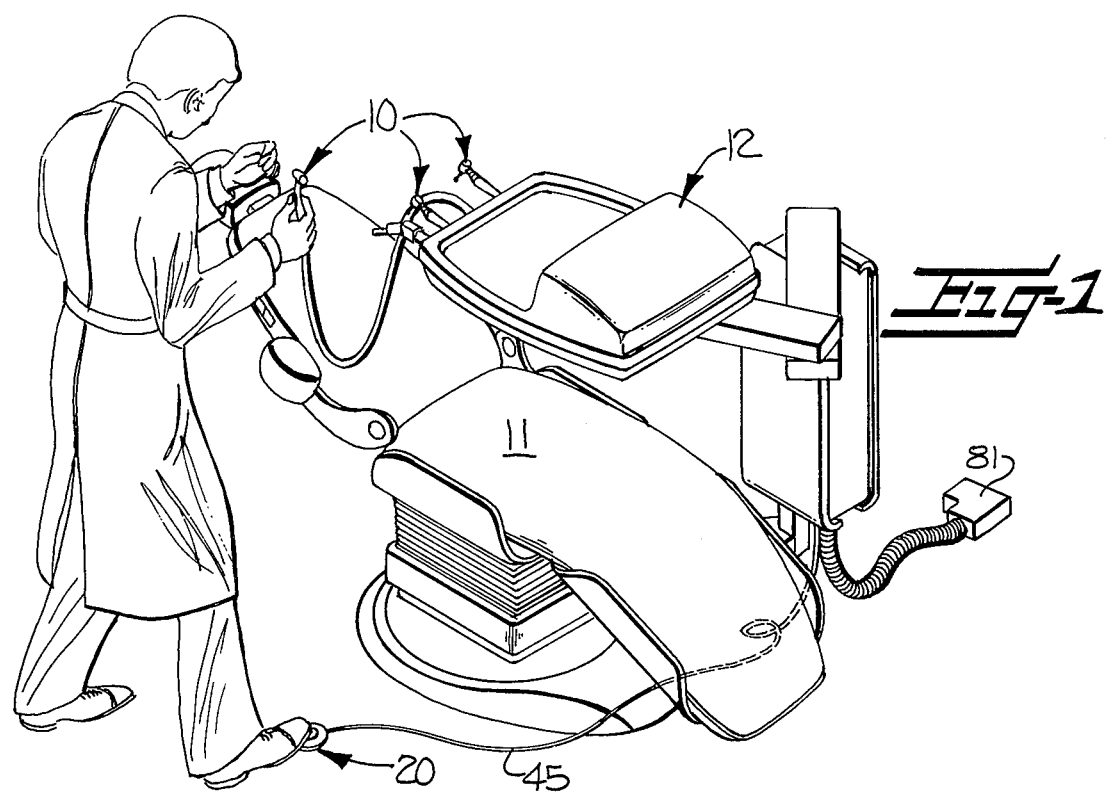

Referring now to the drawings, the foot controller apparatus of this invention is illustrated in FIG. 1 in an environment for manually controlling the supply of compressed drive air to an air driven dental handpiece 10 or the like, and for controlling chip air and coolant water therefor, if utilized. However, it is to be understood that the foot controller apparatus of this invention may be utilized for manually controlling the supply of compressed air to any handpiece instrument or the like and is not necessarily limited to use with the specific air driven dental handpiece illustrated in the drawings.

As may be seen in FIG. 1, a dentist conventionally utilizes air driven dental handpieces 10 for the treatment of a patient positioned in a treatment chair 11. These air driven dental handpieces 10 may be conventionally carried in an over-the-patient instrument console 12 for easy access thereto by the dentist.

The dental handpiece 10 may comprise a conventional air turbine driven dental drill in which the drill portion 13 (see FIGS. 5 and 6) is rotated by an air turbine (not shown) at a speed proportional to the pressure and amount of compressed air supplied to the driving turbine through a drive air conduit 14 which, as shown in FIG. 5, includes two conduits in which the drive air is conveyed to and from the handpiece 10, respectively. These air driven, dental, drill handpieces often also include a nozzle 15 for emitting chip air, coolant water or a mixture of both to be selectively sprayed into the patient's mouth while drilling a tooth. As may be seen in FIGS. 4, 5 and 6, this nozzle 15 includes a water conduit 16 and a chip air conduit 17 telescoped therewithin for selectively supplying the chip air, cooland water or a mixture of both.

Inasmuch as the dentist's hands are usually occupied with both the holding of the handpiece 10 and manipulation of the patient's mouth, control of the drive air, chip air and coolant water to the handpiece 10 should conveniently be performed by the dentist through use of his foot.

In accordance with this invention, a foot controller apparatus is provided for manually controlling the supply of compressed drive air, compressed chip air and coolant water under pressure to the handpiece 10. The foot controller apparatus of this invention is characterized by a construction providing for remote foot control by a minimum size foot pedal device 20 without the necessity of the bulky compressed drive and chip air lines 14, 17 and water line 16 passing through the foot pedal device 20 or the incorporation of complicated electrical or mechanical mechanisms in the foot pedal device 20. The outwardly biased, compressible, foot pedal device 20 is of minimum size for easy contact by the foot of an operator of the dental handpiece and defines therewithin a hollow cavity (see FIG. 3) having a diaphragm means 21 therein for forming an air sealed chamber 22 within the hollow cavity which reduces in volume upon depression of the foot pedal device 20.

Figure 2:
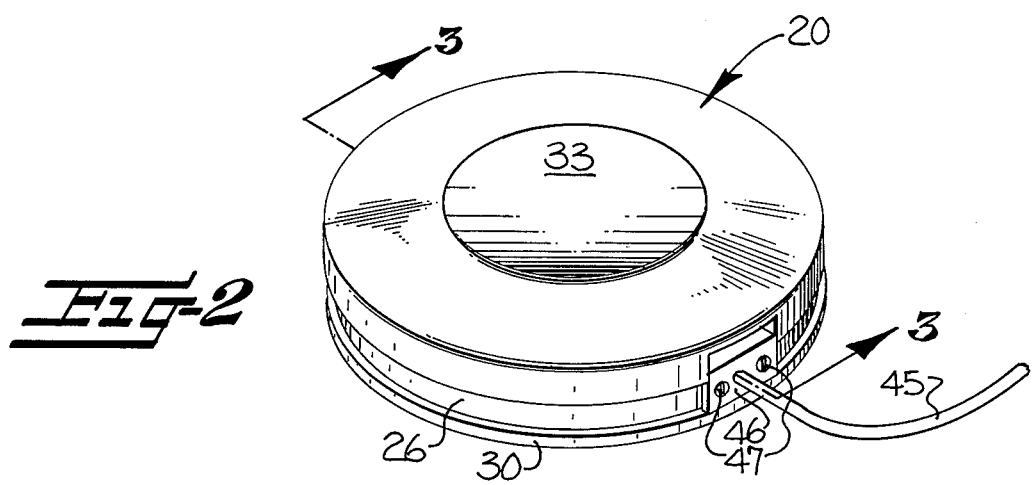
FIG. 2 is an enlarged perspective view of the foot pedal device utilized with the foot controller apparatus of this invention.
Figure 3:
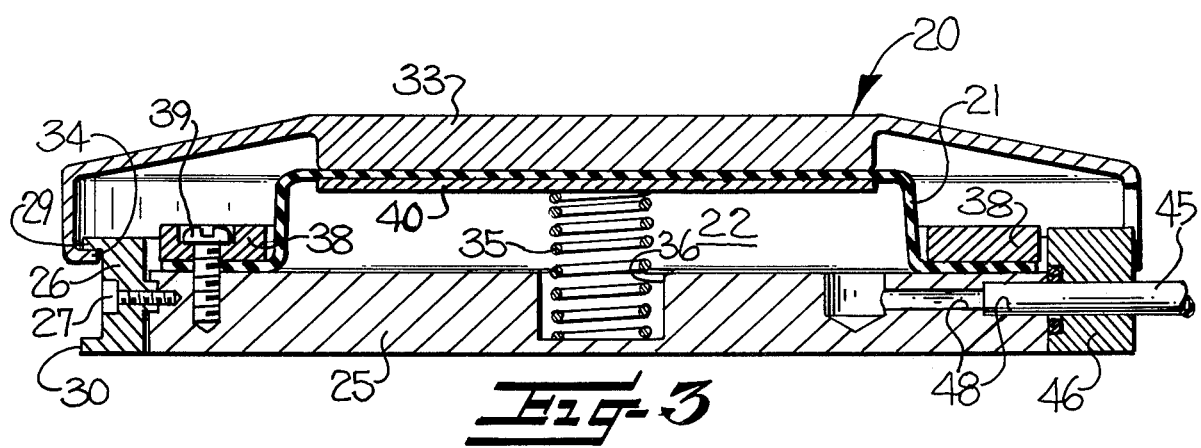
FIG. 3 is a cross-sectional view, taken generally along the line 3—3 of FIG. 2.

The foot pedal device 20, as shown specifically in FIGS. 2, 3 and 8, comprises a base member 25 having a lower surface portion for resting on the floor and being of a generally circular configuration. A collar member 26 in the form of a split ring is secured to the base member 25 by suitable screw members 27 around the outside periphery of the base member 25. The collar member 26 includes outwardly extending upper and lower flange members 29, 30 to form a generally C-shaped configuration. The collar member 26 is upstanding generally from the base member 25 and the flange 29 thereof extends above the upper surface of the base member 25.

The foot pedal device 20 further includes an upper member 33 of circular, generally shallow, inverted cup-shaped configuration having an upper surface of generally circular, convex configuration for being positioned over and around the upstanding collar member 26 for forming with the base member 25 and the collar member 26 the hollow cavity within the foot pedal device 20, as may be seen clearly in FIG. 3.

Retaining means are provided for retaining the upper member 33 on the base member 25 while allowing upward and downward movement of the upper member 33 relative to the base member 25 for reducing and expanding the volume of the above-described hollow cavity within the foot pedal device 20. The retaining means includes the outwardly extending upper flange portion 29 of the upstanding collar 26 and cooperating inwardly extending flange portion 34 extending inwardly from the lower outside periphery of the upper member 33, as shown in FIG. 3, for overlapping the flange 29 of the upstanding collar 26. These cooperating flange portions 29, 34 of the collar member 26 and upper member 33 of the foot pedal device 20 allow upward and downward movement of the upper member 33 relative to the base 25 in the area between the flange portions 29, 30 of the upstanding collar member 26.

For biasing the upper member 33 in the upper extent of its relative movement with respect to the base member 25, a longitudinally-extending spring 35 is positioned between a central portion of the base member 25 and within a recess 36 therein and a central portion of the upper member 33 for exerting an upward force on the upper member 33 to retain it in its upper position until the upper member 33 is pressed downwardly by the foot of the dentist or other person utilizing the handpiece 10.

The foot pedal device 20 further includes the diaphragm member 21 which is generally circular in overall configuration and has a substantially inverted cup shape. The diaphragm member 21 is secured at its outer periphery by ring member 38 and screws 39 to the upper surface of base member 25. The diaphragm member 21 extends over and closes the cavity within said foot pedal device to form the air sealed chamber 22 within the foot pedal device 20. The diaphragm member 21 is attached for movement with the upper member 33 by a plate 40 against which the spring 35 exerts a force to sandwich the central portion of the diaphragm 37 between the plate 40 and the upper member 33, as clearly shown in FIG. 3. Thus, as the upper member 33 is moved up and down relative to the base portion 25, the diaphragm member 37 is also moved up and down for reducing and expanding the volume of the air sealed cavity 22 within the foot pedal device 20.

Due to the above construction of the foot pedal device 20, a slight pressure thereon by the dentist or other person using the handpiece 10 at any portion of the upper surface of the upper member 33 will cause a reduction in volume of the air sealed chamber 22.

The foot controller apparatus of this invention further includes an elongate air tube 45 of smaller cross-sectional dimensions than the compressed air conduit 14 necessary for conveying compressed air to the dental handpiece 10 and being connected at one end with the foot pedal device 20 and communicating with the air sealed chamber 22 therein for conveying an air flow therethrough. For this purpose, one end of the air tube 45 extends through a mounting box 46 which is secured to the outside periphery of the base member 25 of the foot pedal device 20 and is positioned between the split ends of the upstanding collar member 26. The mounting block 46 is secured to the base portion 25 by suitable screws 47 and the air tube 45 extends through the mounting block 46 and communicates with a passageway 48 formed through the base member 25 and extending into the air sealed cavity 22 within the foot pedal device 20.

Thus, as the foot pedal device is depressed by the dentist or other person utilizing the handpiece 10, the air sealed chamber 22 reduces in volume causing an air flow through the passageway 48 to and through the air tube 45.

The foot controller apparatus of this invention further includes a diaphragm operated, air modulating, regulator valve means 50 for being positioned away from the foot pedal device 20 to avoid interference with the dentist or other operator of the handpiece 10. The diaphragm operated valve 50 is positioned in and forms a part of the compressed drive air conduit 14 leading to the handpiece 10 for supplying drive air to the handpiece 10 for driving the air driven drill 13 thereof. The diaphram operated valve 50 is also connected with the other end of the air tube 45 for being pneumatically operated by the flow of air through the air tube resulting from foot operation of the foot pedal device 20 for controlling the flow of compressed drive air to the handpiece 10 for driving same.

The diaphragm operated, air modulating, regulator valve 50 comprises a body portion including an upper body member 51 and a lower body member 52 suitably secured together and defining a hollow cavity 53 therewithin. A generally vertically extending passageway 54 connects with a generally horizontally extending passageway 55 to form an air conveying passageway through the body portion 51 of the diaphragm operated valve 50. The passageway 54 includes a threaded portion in the upper end thereof for receiving the threaded outer end of a coupling member 56 connected to the compressed drive air conduit 14 and the passageway 55 includes a threaded portion for receiving a threaded coupling 57 on the other portion of the compressed drive air conduit 14, as shown in FIG. 7. Thus, the passageways 54, 55 through the body portion 51 of the valve 50 form a part of the conduit 14 for conveying compressed drive air from a source of supply to the handpiece 10.

The passageway 54 includes a tapered portion 59 therein forming a valve seat. The valve 50 further includes a generally tapered valve member 60 which is elongate and has one end thereof extending through the tapered valve seat 59 and into the passageway 54. The valve member 60 is adapted for upward and downward movement, as viewed in FIG. 7, for progressively opening and closing the passageway 54, 55 for progressively allowing a greater flow of compressed air therethrough or for closing the flow of compressed air depending upon the extent of upward movement of the valve member 60, as viewed in FIG. 7.

The valve member 50 includes a diaphragm member 64 extending across the hollow cavity 53 and secured at its outer periphery between the valve body members 51, 52, as shown in FIG. 7. On one side of the diaphragm member 64, a passageway 65 is formed through the valve body 52 and includes a threaded portion for receiving a threaded coupler member 66 connected with the air tube 45 so that a flow of air comes into the valve body member 52 through the passageway 65 and against one side of the diaphragm member 64 in an air sealed portion of the valve body cavity 53. The diaphragm member 64 includes a block or piston member 67 on the other side thereof which is secured to the lower end of the valve member 60 and is therefore biased in a downward position by the flow of compressed air acting against the top of the valve member 60.

Thus, the valve member 60 is biased in a closed position, as illustrated in FIG. 7, by the pressure of the compressed air against the top thereof. However, when the dentist or other user of the handpiece 10 depresses the foot pedal device 20 causing a flow of air through the air tube 45, this flow of air will move the diaphragm member 64 and the piston member 67 in an upward direction, as viewed in FIG. 7, to move the valve member 60 progressively upwardly to allow a flow of compressed drive air through the valve member 50 proportionate to the amount of depression of the foot pedal device 20. For example, the more the foot pedal device 20 is depressed the greater the reduction in the volume of the air sealed chamber therein and the greater the air flow through the air tube 45 to the diaphragm member 64 in the valve 50. Since this a closed pneumatic system, the diaphragm member 64 in the valve 50 will be moved upwardly to a proportionate extent of the depression of the foot pedal device 20 to proportionately open the valve member 60 with respect to the valve seat 59 for progressively allowing a greater flow of compressed drive air through the valve 50 for controlling the speed of operation of the drill 13 of the handpiece 10.

The foot controller apparatus of this invention may further include a diaphragm operated electrical switch 70 which is positioned away from the foot pedal device 20 to avoid interference with the operator of the dental handpiece and is electrically connected through a suitable electronic control circuit 71 with electrically operated valves 72, 73 in the chip air conduit 17 and the coolant water conduit 16. The diaphragm operated electrical switch 70 is pneumatically connected with the air tube 45 from the foot pedal device 20 for being pneumatically operated by the flow of air through the air tube 45 resulting from foot operations of the foot pedal device 20 for electrically controlling the flow of chip air and coolant water to the dental handpiece.

As shown in FIGS. 4 and 9, the diaphragm operated electrical switch 70 includes upper and lower housing members 74, 75 forming a hollow cavity 76 therewithin and having a diaphragm member 77 extending across the hollow cavity 76. The air tube 45 or an extension thereof, as illustrated in FIGS. 4 and 7, is connected with the bottom of the cavity 76 in the body portion 74, 75 of the diaphragm operated switch 70 for providing a flow of air on one side of the diaphragm 77. Connected to or resting against the other side of the diaphragm 77 is a plunger member 79 which is connected with an electrical switch 80 for opening and closing the electrical switch 80 depending upon the flow of air through tube 45. The switch 80 is electrically connected by the electronic control circuit 71 which is in turn electrically connected with the valves 72, 73 in the chip air and water conduits 17, 16 for controlling the flow of chip air and coolant water out of the nozzle 15 in the end of the handpiece 10.

The electronic circuit 71, which need not be described herein, may be suitably constructed for controlling chip air and coolant water in any desired combination depending upon actuation of the switch 80. For example, the electronic circuit 71 may be so constructed that the switch 80 need be closed a predetermined number of times for actuation of one or the other or both of the valves 71, 72 for allowing the flow of chip air, coolant water or both.

The diaphragm operated electrical switch 70 may be secured to the body portion 51, 52 of the diaphragm operated air modulating regulator valve 50 or may be separate therefrom, as schematically illustrated in the drawings. However, in the concept of this invention, both the air modulating valve 50 and the diaphragm operated electrical switch 70 should be positioned at a location remote from the foot pedal device 20, such as within the console 12, so as to maintain the foot pedal device 20 of a minimum size to avoid interference with mobility of the dentist or other user of a handpiece 10.

As illustrated schematically in FIG. 4, the water and air supply may be positioned under the floor of the room in which the equipmemnt of this invention is being utilized and conveyed through suitable conduits through a valve box 81 having valves therein for controlling the flow of air and water. These main air and water conduits eventually lead to the above-identified drive air, chip air and coolant water conduits for control by the foot controller apparatus of this invention. Other suitable switches and valves are employed in these conduits for desired control of the handpiece 10, as may be desired.

The foot controller apparatus of this invention manually controls the supply of compressed drive air to an air driven dental handpiece or the like and may control chip air and coolant water, if utilized, and is characterized by a construction providing for remove foot control by a minimum size foot pedal device 20 without the necessity of the bulky compressed air and water lines, if utilized, passing through the foot pedal device 20 or the incorporation of complicated electrical or mechanical mechanisms in the foot pedal device 20.

In the drawings and specification, there has been set forth a preferred embodiment of the invention and, although specific terms are employed, they are used in a generic and descriptive sense only.

What is claimed is:

1. Foot controller apparatus for manually controlling the flow through a supply line to a dental handpiece or the like and being characterized by a construction providing for remote foot control by a minimum size foot pedal device of the flow through the supply line to a handpiece without the necessity of bulky compressed air lines passing through the foot pedal device or the incorporation of complicated electrical or mechanical mechanisms in the foot pedal device; said foot controller apparatus comprising:

a foot pedal device of minimum size for easy contact by the foot of an operator of the dental handpiece and comprising a base member having a lower surface portion for resting on a floor, an upper member of generally shallow inverted cup-shaped configuration for being positioned over and around said base member for forming with said base member a hollow cavity within said foot pedal device, retaining means for retaining said upper member on said base member while allowing upward and downward movement of said upper member relative to said base member, biasing means positioned between said upper member and said base member for biasing said base member upwardly while allowing depression of said upper member relative to said base member, and a diaphragm member secured around its periphery to said base member and being attached to said upper member for movement therewith and extending over and closing said cavity within said foot pedal device to form a fluid sealed chamber which reduces in volume upon depression of said foot pedal device;

an elongate tube of small cross-sectional dimensions being connected at one end thereof with said foot pedal device and communicating with said fluid sealed chamber for conveying a flow of fluid therethrough resulting from operation of said foot pedal device; and fluid-responsive means for being positioned away from said foot pedal device to avoid interference with the operator of the dental handpiece and operatively connected with the supply line and with the other end of said fluid tube for being operated by the flow of fluid through said fluid tube resulting from foot operation of said foot pedal device for controlling the flow through the supply line to the dental handpiece.

2. Foot controller apparatus, as set forth in claim 1, in which
said upper member of said foot pedal device includes an upper surface of generally circular, convex configuration, and
said biasing means comprises a longitudinally-extending spring member extending between central portions of said base member and said upper member, whereby, an operator of the handpiece may place his foot on any convenient portion of said upper surface of said upper portion of said foot pedal device for easily operating said foot controller apparatus.

3. Foot controller apparatus, as set forth in Claim 1, in which said retaining means comprises
a collar member secured to said base member and upstanding from said lower surface thereof for being positioned within said upper member, and
flange means extending outwardly from the upper surface of the periphery of said collar member and inwardly from the periphery of said upper member for overlapping each other.

4. Foot controller apparatus for manually controlling the supply of compressed air to an air-driven dental handpiece or the like and being characterized by a construction providing for remote foot control by a minimum size foot pedal device of the flow of the compressed air from a supply, through an air conduit, to the handpiece without the necessity of bulky compressed air lines passing through the foot pedal device or the incorporation of complicated electrical or mechanical mechanisms in the foot pedal device; said foot controller apparatus comprising:
a foot pedal device of minimum size for easy contact by the foot of an operator of the dental handpiece and comprising a base member having a lower surface portion for resting on a floor, an upper member of generally shallow inverted cup-shaped configuration for being positioned over and around said base member for forming with said base member a hollow cavity within said foot pedal device, retaining means for retaining said upper member on said base member while allowing upward and downward movement of said upper member relative to said base member, biasing means positioned between said upper member and said base member for biasing said base member upwardly while allowing depression of said upper member relative to said base member, and a diaphragm member secured around its periphery to said base member and being attached to said upper member for movement therewith and extending over and closing said cavity within said foot pedal device to form an air sealed chamber which reduces in volume upon depression of said foot pedal device;
an elongate tube of smaller cross-sectional dimensions than the compressed air conduit necessary for conveying compressed air to the dental handpiece and being connected at one end thereof with said foot pedal device and communicating with said air sealed chamber for conveying an air flow of fluid therethrough resulting from operation of said foot pedal device; and
a diaphragm operated, air modulating, regulator valve for being positioned away from said foot pedal device to avoid interference with the operator of the dental handpiece and operatively connected with the supply line and in the compressed air line leading to the dental handpiece, said diaphragm operated valve means being connected with the other end of said air tube for being pneumatically operated by the flow or air through said air tube resulting from foot operation of said foot pedal device for controlling the flow of compressed air to the dental handpiece.

5. Foot controller apparatus, as set forth in claim 4, in which said diaphragm operated, air modulating, regulator valve means comprises
a body portion,
a passageway through said body portion for connection with the compressed air conduit of the dental handpiece for forming a part of the conduit and including a tapered portion therein forming a valve seat,
a generally tapered valve member having one end thereof extending through said tapered portion forming said valve seat and cooperating therewith for movement in a direction opposite to the flow of compressed air through said passageway and between a position closing said passageway to prevent the flow of compressed air therethrough and positions allowing progressively greater flow of compressed air therethrough,
a hollow cavity defined within said body portion and connected at one side with said other end of said air tube from said foot pedal device, and
diaphragm means extending across said hollow cavity at generally the other side thereof and being connected with said valve member for moving said valve member between the aforesaid positions thereof;
whereby, depression of said foot pedal device causes an air flow through said air tube to said hollow cavity of said regulator valve for moving said valve diaphragm means to move said valve member to allow a flow of compressed air to the dental handpiece proportionate to the amount of depression of said foot pedal device.

6. Foot controller apparatus for manually controlling the supply of compressed air to an air driven dental handpiece or the like and being characterized by a construction providing for remote foot control by a minimum size foot pedal device of the flow of the compressed air from a supply, through an air conduit, to the dental handpiece without the necessity of bulky compressed air lines passing through the foot pedal device or the incorporation of complicated electrical or mechanical mechanisms in the foot pedal device; said foot controller apparatus comprising:
a foot pedal device of minimum size for easy contact by the foot of an operator of the dental handpiece and comprising a base member having a lower surface portion for resting on a floor, a collar member secured to said base member and upstanding from said lower surface portion thereof, an upper member of generally shallow, inverted cup-shaped configuration having an upper surface of generally circular, convex configuration for being positioned over and around said upstanding collar member for forming with said base member and said collar member a hollow cavity within said foot pedal device, retaining means for retaining said upper member on said base member while allowing upward and downward movement of said upper member relative to said base member and comprising flange means extending outwardly from the upper surface of the periphery of said collar member and inwardly from the periphery of said upper member for overlapping each other, longitudinally-extending spring means extending between central portions of said base member and said upper member for biasing said base member upwardly to the position of engagement of said flange means while allowing upward and downward movement of said upper member relative to said base member, and a diaphragm member secured around its periphery to said base member and extending over and closing said cavity within said foot pedal device to form an air sealed chamber and being attached to said upper member for movement therewith;

an elongate tube of smaller cross-sectional dimensions than the compressed air conduit necessary for conveying compressed air to the dental handpiece, and being connected at one end thereof with said foot pedal device and communicating with said air sealed chamber for conveying an air flow therethrough; and an air modulating, regulator valve for being positioned away from said foot pedal device to avoid interference with the operator of the dental handpiece and in the compressed air conduit leading to the dental handpiece and comprising a body portion, a passageway through said body portion for connection with the compressed air conduit of the dental handpiece for forming a part of the conduit and including a tapered portion therein forming a valve seat, a generally tapered valve member having one end extending through said tapered portion forming said valve seat and cooperating therewith for movement in a direction opposite to the flow of compressed air through said passageway and between a position closing said passageway to prevent the flow of compressed air therethrough and positions allowing progressively greater flow of compressed air therethrough, a hollow cavity defined within said valve body portion and connected at one side with the other end of said air tube extending from said foot pedal device, and diaphragm means extending across said valve cavity at generally the other side thereof and being connected with said valve member for moving said valve member between the aforesaid positions thereof; whereby, depression of said upper member of said foot pedal device against the bias of said spring reduces the volume of said foot pedal device chamber to cause a proportionate flow of air through said tube to said valve cavity for moving said valve diaphragm means to move said valve member to allow a flow of compressed air to the dental handpiece proportionate to the amount of depression of said foot pedal device for driving the dental handpiece at a desired speed.

7. In an air driven dental handpiece mechanism or the like instrument having a supply of compressed air, a conduit for conveying the compressed air to the handpiece for driving same, and means in said handpiece for emitting chip air and coolant water including a water supply, a conduit for conveying water to said handpiece, a separate conduit for conveying compressed air to said handpiece and electrically operated valve means in said chip air conduit and said coolant water conduit; the combination therewith of, foot controller apparatus for manually controlling the supply of drive air, chip air, and coolant water to said handpiece and being characterized by a construction providing for remote foot control by a minimum size foot pedal device without the necessity of bulky compressed air lines passing through the foot pedal device or the incorporation of complicated electrical or mechanical mechanisms in the foot pedal device, said foot controller apparatus comprising:

an outwardly biased, depressible foot pedal device of minimum size for easy contact by the foot of an operator of the dental handpiece and defining therewithin a hollow cavity having a diaphragm means therein for forming an air sealed chamber which reduces in volume upon depression of said foot pedal device;

an elongate tube of smaller cross-sectional dimensions than the compressed air conduit necessary for conveying compressed air to the dental handpiece, and being connected at one end thereof with said foot pedal device and communicating with said air sealed chamber for receiving an air flow therethrough resulting from operation of said foot pedal device;

a diaphragm operated, air modulating, regulator valve means for being positioned away from said foot pedal device to avoid interference with the operator of the handpiece and in said drive air conduit leading to said dental handpiece, said diaphragm operated valve means being connected with said air tube for being pneumatically operated by the flow of air through said air tube resulting from foot operation of said foot pedal device for controlling the flow of drive air to said dental handpiece; and diaphragm operated electrical switch means positioned away from said foot pedal device to avoid interference with the operator of the dental handpiece and electrically connected with said electrically operated valve means in said chip air and coolant water conduits, said diaphragm operated switch means being connected with said air tube for being pneumatically operated by a flow of air through said air tube resulting from foot operation of said foot pedal device for electrically operating said valve means to control the flow of chip air and coolant water to said dental handpiece.

8. In a dental handpiece mechanism, as set forth in claim 7, in which said foot pedal device comprises a base member having a lower surface portion for resting on a floor, a collar member secured to said base member and upstanding from said lower surface portion thereof, an upper member of generally shallow, inverted cup-shaped configuration having an upper surface of generally circular, convex configuration for being positioned over and around said upstanding collar member for forming with said base member and said collar member a hollow cavity within said foot pedal device, retaining means for retaining said upper member on said collar member while allowing upward and downward movement of said upper member relative to said base member, and longitudinally-extending spring means extending between central portions of said base member and said upper member for biasing said base member upwardly while allowing upward and downward movement of said upper member relative to said base member; and said diaphragm means comprises a diaphragm member secured around its periphery to said base member and extending over and closing said cavity within said foot pedal device to form a said air sealed chamber and being attached to said upper member for movement therewith; whereby, an operator of the dental handpiece may depress said upper member to a desired degree against the bias of said spring means for depressing said diaphragm member to reduce the volume of said air sealed chamber to cause a proportionate flow of air through said tube to said air modulating valve and said diaphragm operated electrical switch means for causing a desired flow of compressed air through said air modulating valve for driving said dental handpiece at a desired speed and for providing chip air and coolant water to said dental handpiece.

9. In a dental handpiece mechanism, as set forth in claim 7, in which said diaphragm operated, air modulating, regulator valve means comprises a body portion, a passageway through said body portion for connection with said drive air conduit of said handpiece for forming a part of said conduit and including a tapered portion therein forming a valve seat, a generally tapered valve member having one end thereof extending through said tapered portion forming said valve seat and cooperating therewith for movement in a direction opposite to the flow of drive air through said passageway and between a position closing said passageway to prevent the flow of drive air therethrough and positions allowing progressively greater flow of drive air therethrough, a hollow cavity defined within said body portion and connected at one side with said air tube from said foot pedal device, and diaphragm means extending across said hollow cavity at generally the other side thereof and being connected with said valve member for moving said valve member between the aforesaid positions thereof;

whereby, depression of said foot pedal device causes an air flow through said air tube to said hollow cavity of said regulator valve for moving said valve diaphragm means to move said valve member to allow a flow of drive air to said dental handpiece proportionate to the amount of depression of said foot pedal device.

* * * * *

UNITED STATES PATENT AND TRADEMARK OFFICE
CERTIFICATE OF CORRECTION

PATENT NO. : 4,114,275
DATED : September 19, 1978
INVENTOR(S) : Jones et al

It is certified that error appears in the above-identified patent and that said Letters Patent are hereby corrected as shown below:

Column 1, Line 14, delete "in"; Column 2, Line 19, change "lins" to --lines--; Column 3, Line 59, change "conventionally" to --conveniently--; Column 4, Line 8, change "cooland" to --coolant--; Column 5, Line 57, insert --and-- after "48"; Column 8, Line 10, change "remove" to --remote--; Column 8, Line 25, change "a" to --the--; Column 10, Line 3, change "or" to --of--.

Signed and Sealed this

Second Day of January 1979

[SEAL]

Attest:

RUTH C. MASON
Attesting Officer

DONALD W. BANNER
Commissioner of Patents and Trademarks